United States Patent [19]

Martz

[11] Patent Number: 4,793,803
[45] Date of Patent: Dec. 27, 1988

[54] REMOVABLE TOOTH POSITIONING APPLIANCE AND METHOD

[76] Inventor: Martin G. Martz, 215 S. Monarch St., Aspen, Colo. 81611

[21] Appl. No.: 105,914

[22] Filed: Oct. 8, 1987

[51] Int. Cl.$^4$ ............................................. A61C 7/00
[52] U.S. Cl. ....................................................... 433/6
[58] Field of Search ........................................ 433/6, 7

[56] References Cited

U.S. PATENT DOCUMENTS

| | | | |
|---|---|---|---|
| 3,510,946 | 5/1970 | Kesling | 433/6 |
| 4,055,895 | 11/1977 | Huge | 433/6 |
| 4,505,672 | 3/1985 | Kurz | 433/6 |
| 4,541,800 | 9/1985 | Bernstein | 433/6 |
| 4,591,341 | 5/1986 | Andrews | 433/6 |

*Primary Examiner*—Robert Peshock
*Attorney, Agent, or Firm*—Julian Caplan

[57] ABSTRACT

Separate appliances are insertable in and removable from the upper and lower jaws of the patient to correct minor malocclusions. The appliance construction has several modifications but consists essentially of: (a) a fairly rigid portion which mates with or securely grips the tooth surface, (b) a rigid portion to provide the base and shape, and (c) an intermediate, flexible resilient portion interposed between (a) and (b) which biases the teeth into the desired position. Details and variations of each of the three portions are described. The rigidity of the rigid portion may vary depending on the condition of an individual case. In some instances the rigid portion need only be somewhat flexible, thereby performing the function of the intermediate portion as well. The method of fabricating each portion is likewise disclosed.

44 Claims, 8 Drawing Sheets

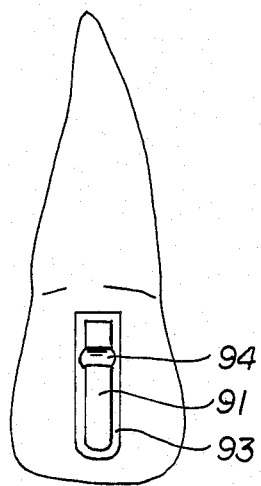
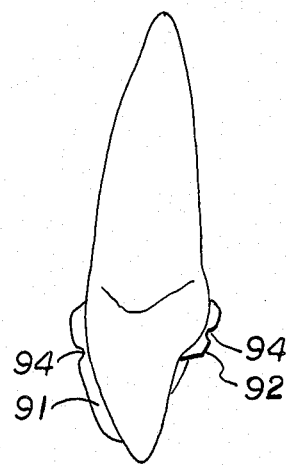
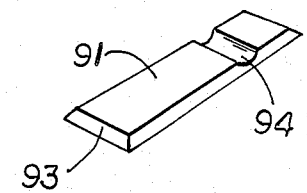
Fig.20    Fig.20a    Fig.20b
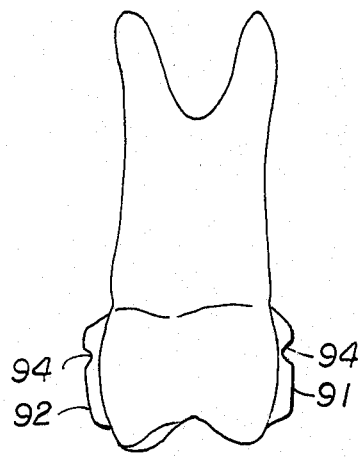
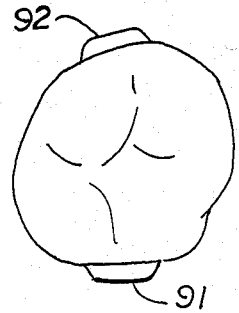
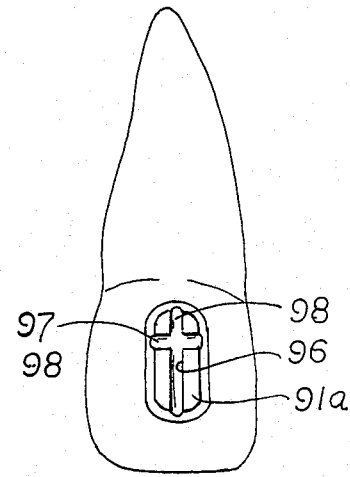
Fig.20c    Fig.20d    Fig.21
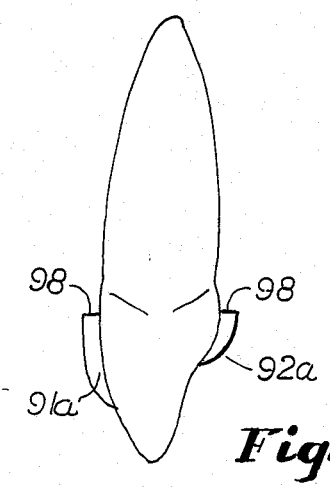
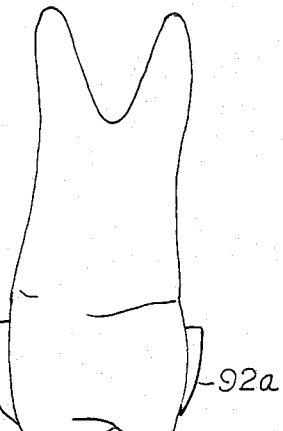
Fig.21a    Fig.21c    Fig.21b    Fig.21d

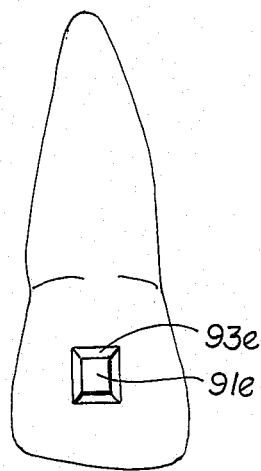# 
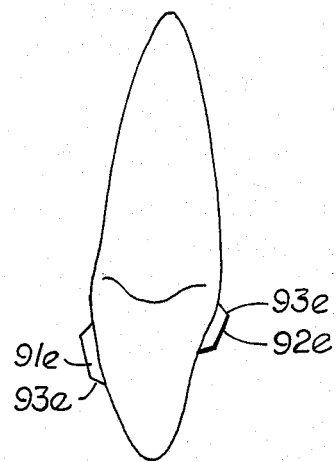
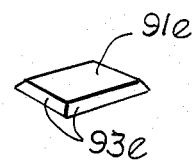
Fig.25  Fig.25a  Fig.25b
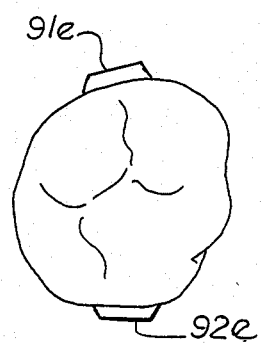
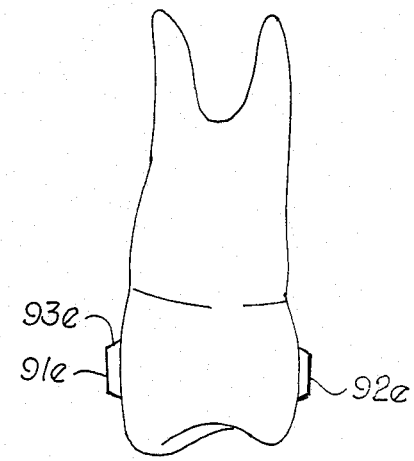
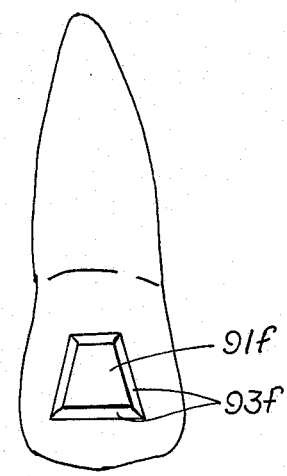
Fig.25d  Fig.25c
Fig.26

REMOVABLE TOOTH POSITIONING APPLIANCE AND METHOD

BACKGROUND OF THE INVENTION

1. Field of the Invention

This invention relates to a new and improved removable orthodontic appliance, namely, a tooth repositioning appliance and method. The present invention expands the range of treatments for minor malocclusions by allowing the orthodontist to shift the position of the teeth within the upper or lower arch a greater distance and also to move one dental arch relative to the other. Deep overbites or open bites may also be corrected. The invention enables the orthodontist to treat more severely malposed teeth than is possible with prior removable orthodontic "finishing" appliances. A feature of the invention is the fact that it is removable and the patient himself can remove and replace the appliances.

2. Description Of Related Art

Removable orthodontic appliances are old in the art as are two piece appliances. U.S. Pat. No. 4,505,672 discloses upper and lower appliances for the upper and lower jaws and mechanical clasps and/or suction cups to attach the appliances to the teeth. Resilient means interconnect the two appliances. The present invention differs from the disclosure of such patent in a number of respects, one being that the use of clasps that grip between the teeth frequently opening up a gap between teeth is not employed. The present invention uses clasp assemblies which firmly grip individual teeth. The guides and guideways in such reference limit the effectiveness of the positioner; a feature of the present invention is that such guides and guideways are not required.

Single piece appliances which fit on both the upper and lower jaw are shown in patents to Kesling, such as U.S. Pat. Nos. 4,330,273; 4,195,046; 3,837,081; 3,724,075; and 3,178,820. See also, *Practical Application of the Kesling Tooth Positioner* by Peter C. Kesling, D.D.S. Positioners of this type are formed of an elastic material about the arches in a slightly open position. The elasticity of the material in the positioners puts pressure on the teeth biasing them from their present position to the new, ideal position as the appliance is seated. Single piece appliances suffer from the severe limitation that when the patient's jaw muscles are relaxed, the device is not effective. One of the features of the present invention is the fact that there are two separate positioners, one for the upper and one for the lower jaw and each positioner locks onto the undercuts of the teeth, whether natural or enhanced by bonded additions.

In the main, other tooth positioning appliances heretofore used in the orthodonture profession have been permanent appliances which are adjusted from time to time by the orthodontist but otherwise remain fixed to the teeth. A feature of the present invention is the fact that the device may be removed as required and particularly when the patient is speaking. Nevertheless, the appliances may be worn while sleeping without undue discomfort.

SUMMARY OF THE INVENTION

Each of the two appliances consists essentially of three separate portions and the portions are themselves subject to considerable variation. Thus, one portion is fairly rigid and grips the teeth and holds the appliance in place during use but is sufficiently flexible so that the patient can remove the appliance when desired. A second portion is more rigid and forms a backbone which maintains the desired shape of the dental arch. The third portion is intermediate the first two and is resilient and is preset to bias the teeth within the upper and lower arch, or both, to the desired final position. Inter-arch movement is also achieved by the use of resilient elastic members connecting the upper jaw and lower jaw positioners.

IN THE DRAWINGS

The invention and objects and features thereof will be more readily apparant from the following detailed description and appended claims when taken with the drawings, in which:

FIG. 20 is a front elevational view of a tooth to which a button in accordance with the present invention is applied, the tooth being a maxillary central incisor.

FIG. 20A is a side elevation thereof.

FIG. 20B is a perspective view of one of the buttons applied in FIG. 20.

FIG. 20C is a side elevational view similar to FIG. 20A showing the device applied to a bicuspid.

FIG. 20D is a plan view showing the device applied to a first molar.

FIG. 21 is a view similar to FIG. 20 showing a modified button.

FIG. 21A is a view similar to FIG. 20A.

FIG. 21B is a side elevational view of one of the buttons of FIG. 21A.

FIG. 21C is a side elevational view of the other button shown in FIG. 21A.

FIG. 21D is a view similar to FIG. 20C showing the device of FIG. 21.

FIG. 25B is a view similar to FIG. 20 of another modification.

FIG. 25A is a view similar to FIG. 20A of the modification of FIG. 25.

FIG. 25B is a view similar to FIG. 20B of the modification of FIG. 25.

FIG. 25C is a view similar to FIG. 20C; and

FIG. 25D is a view similar to FIG. 20D of the modification of FIG. 25.

FIG. 26 is a view similar to FIG. 20 of a still further modification.

DESCRIPTION OF PREFERRED EMBODIMENTS

The elastic positioners of the present invention are separate single units for the upper and lower jaws molded of rubber, elastomeric material or thermoplastic or other suitable materials which cover the upper and lower teeth simultaneously and hold the jaws in a slightly opened position. The units may also be used one at a time. The material of the appliance contacts almost completely the facial, occlusal and lingual surfaces of the teeth. Additionally, a flange of the material may cover but not contact a portion of the gum tissue all the way around the upper and lower dental arches of both the facial and lingual sides. In some instances, cutouts of the material between teeth may be made to provide additional flexibility.

The positioners are not molded from casts of the teeth in their present, improper positions but rather, from an ideal tooth position "setup" made by a dental laboratory technician.

Preliminarily, the dentist makes plaster casts of the upper and lower teeth in their present or minor malocclusion condition. Also, a tracing of a lateral view skull radiograph for locating the jaw hinge axis position is made. These materials are sent to a dental laboratory or, alternatively, a face-bow recording is made. The laboratory technician takes impressions of the existing casts and makes duplicate plaster casts.

The duplicate plaster casts are mounted in an articulator (commercially available) which allows the casts to be moved and manipulated in a way which simulate the actual jaw movements of the patient.

The hinge axis location of the patient can be duplicated fairly accurately using the articulator and the hinge axis tracing or a face-bow recording.

To prepare a positioner for the upper jaw, the technician cuts apart the plaster casts by making horizontal cuts above the teeth and vertical cuts between the teeth from above until he is very close to the contact point between adjacent teeth. The final separation of the teeth is made by breaking the plaster so that the plaster teeth are not diminished in size by a saw cut. The plaster teeth are then arranged into the desired position and held in place by wax. The technician uses judgment and experience to know how far the teeth may be moved and what types of movements can reasonably be accomplished by the positioner appliance. To prepare a positioner for the lower jaw, the aforementioned horizontal cuts are made above the teeth.

From the ideal wax setup of the plaster teeth, the positioners of the present invention are made. As time goes on, movement of the teeth may be accomplished through multiple stages of the appliance by utilizing more than one wax setup.

Figure 1:
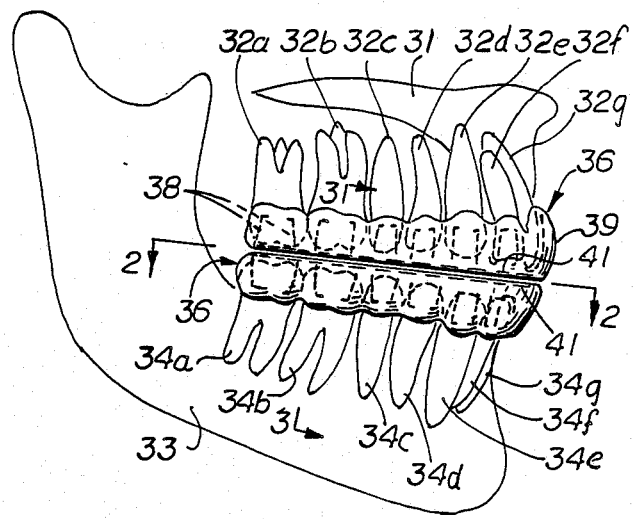
FIG. 1 is a side elevational view of a jaw in which one form of the present invention is installed.
Figure 2:
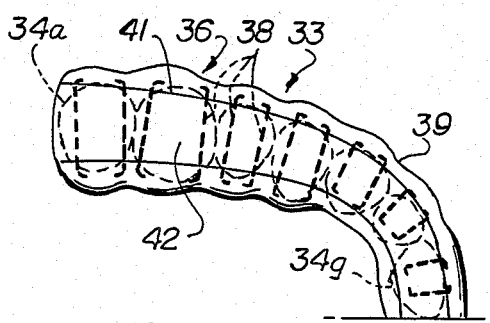
FIG. 2 is a view of a portion of the lower jaw taken substantially along the line 2—2 of FIG. 1 with parts broken away for clarity of explanation.
Figure 3:
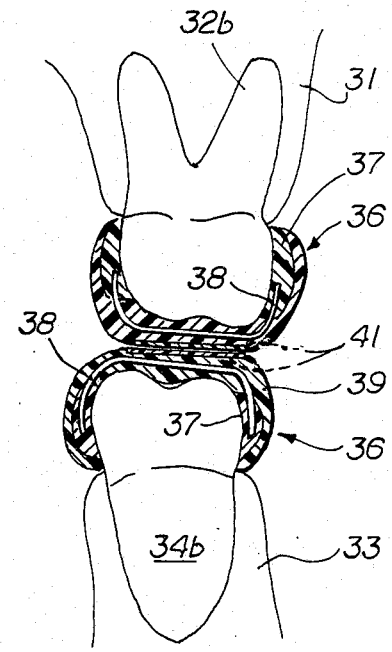
FIG. 3 is a sectional view taken substantially along the line 3—3 of FIG. 1.

Directing attention first to the drawings FIGS. 1-3, there are shown schematically upper jaw 31 and lower jaw 33. The teeth 32 of the upper jaw 31 are designated serially 32a-g while those of the lower jaw are designated 34a-g. As shown in the drawings the teeth are very regular in position. At the outset of the treatment, the teeth are irregular but the positions shown in the accompanying drawings are the ideal or objective of use of the appliances.

There is a separate appliance 36 for each jaw. Each appliance 36 has a tooth clasp portion 37 which detachably engages the teeth so that the user may install and remove the appliance as required. In the form of the invention shown in FIGS. 1-3, the tooth clasp portion 37 may be augmented by spring tension wires 38. The material of construction of clasp portion 37 preferably is a hard plastic and the spring wires 38 reinforce the plastic. Alternatively, this portion of the appliance may be of metal or other substances.

Joined to the clasp portion 37 is a flexible intermediate portion 39 which is quite flexible and resilient. The shape of the intermediate portion 39 depends upon movements needed for specific teeth.

There is a backbone portion 41 which provides the basic arch shape and is preferably made of a plastic material which is more rigid than intermediate portion 39 and having a preferably flat occlusal surface 42. The properties of the material used depends on the required movement of teeth for the individual patient. The function of the intermediate portion 39 is to bias the clasp portion 37 to exert continuous pressure on the teeth to move teeth to the desired final position. Thus, the backbone 41 constitutes an abutment against which the intermediate portion 39 may push or pull to bias the tooth clasp portion 37 and the teeth engaged thereby into the desired final position.

Each of the three portions of the appliance 36 is subject to certain modifications. In general, the elastic properties of the materials are selected based upon the needs of the particular malocclusion present.

Each unit has an occlusal or biting surface 42 which is approximately a flat plane surface where it comes into contact with the opposing unit. The surface need not be absolutely flat as the appliance is clipped on the teeth but may follow the contours of the dental arch as the material is flexed. Openings may be placed in the occlusal surface to allow the contact of some or all of the upper and lower teeth. In some cases, no occlusal coverage may be needed but the functions of the backbone or attachment or intermediate sections may be met by other means.

The upper and lower units may be moved relative to each other by suitable force application methods. Attachments may be placed on either the upper or lower units or both to provide a place for connecting elastic bands, springs, headgear type traction appliances, magnets, screw type force applicators and the like. Movement of the teeth may be accomplished through multiple stages of the appliance by utilizing more than one wax setup. If the movements desired are more than the resilience of the material can provide, or more force would be applied to the teeth than can be tolerated within the range of normal orthodontic tooth movement physiology, then multiple setups and appliances may be used. Parts of the appliance may be combined with other types of orthodontic appliances to accomplish more extreme tooth movements.

The tooth clasp portion 37 is custom fitted to the facial and lingual surfaces of the patient's teeth. The intermediate portion 39 of flexible urethane plastic, rubber or other material is molded to fit over and around the clasp assemblies and to come between the clasps and the backbone part of the appliance. This intermediate portion 39 provides the energy to move the teeth. As the appliance is seated on the teeth, the material is deformed and the spring force of the material trying to return to its original shape provides the force to straighten the teeth. The backbone material 41 is a more rigid plastic and holds to the basic arch shape of the appliance. The backbone material may be sufficiently deformable to supply additional energy to move teeth.

Figure 4A:
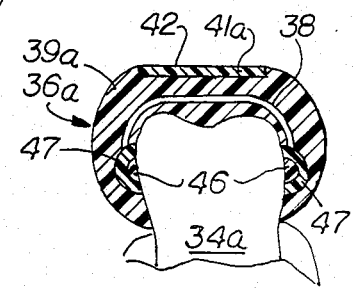
FIG. 4a is a view similar to FIG. 4 of a modification.
Figure 4:
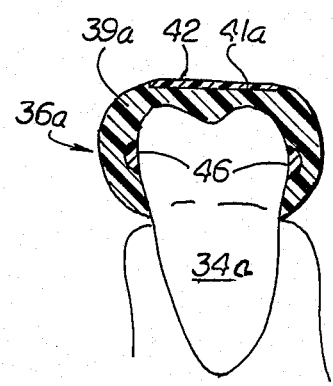
FIG. 4 is a modification of a portion of FIG. 3.

FIG. 4 is a view similar to FIG. 3 of a modification wherein the wires 38 which assist in holding the tooth clasp portions 37 of the preceding modification in place are eliminated. Buttons 46 are bonded onto the teeth to increase natural undercuts. Buttons 46 may be of a transparent dental composite material that is drilled, sanded or otherwise shaped using standard dental procedures to the desired contours. Premolded standardized buttons of any suitable material may be bonded to the teeth using dental adhesives. Placement of the buttons may be performed prior to taking the impressions for the master casts sent to the laboratory. In other respects the modification of FIG. 4a resembles that of the preceding modification and the same reference numerals followed by the subscript are used to designate corresponding elements.

Figure 7:
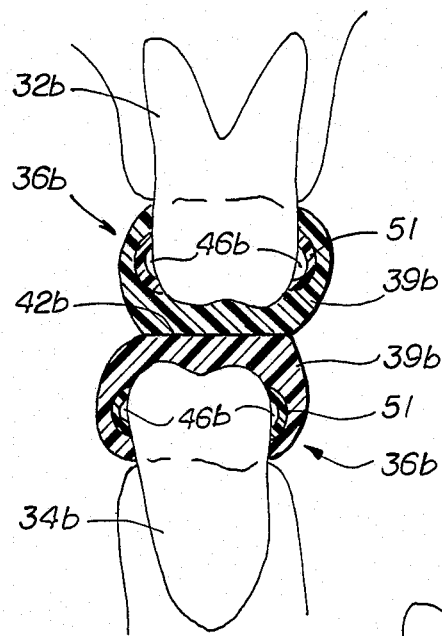
FIGS. 5, 6 and 7 are views similar to FIGS. 1, 2 and 3 of a further modification.
Figure 6:
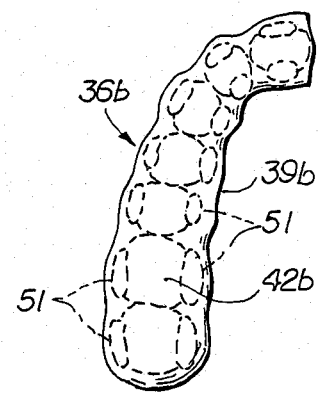
Figure 5:
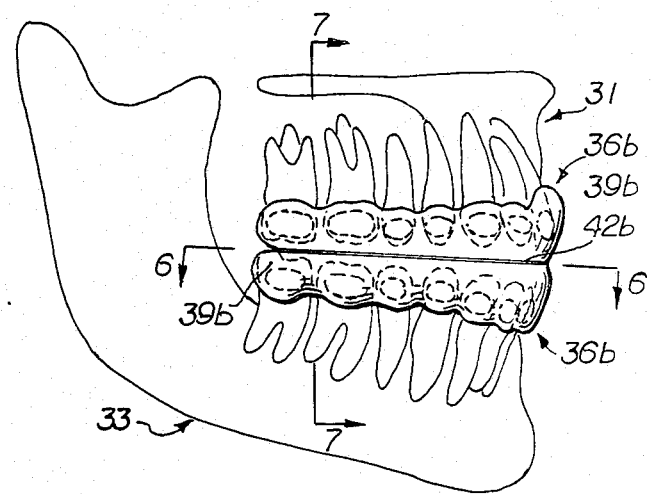

FIGS. 5-7 illustrate another modification. Rigid caps 51 are shaped concave to precisely mate with buttons 46b, which are bonded to the teeth as in FIG. 4. Caps 51 are bonded or held fixedly in place relative to flexible intermediate material 39b. The intermediate material portion 39b forms the entire body of the appliance and no backbone stiffening similar to reference numeral 41 of the preceding modifications is required. Neither are metal springs required in the clasps In the modification shown in FIG. 4A, buttons 46 are bonded onto teeth to increase the undercuts and to facilitate clasp portions 47 attached to opposite ends of wires 38 gripping the teeth more effectively. As stated, the buttons 46 may be of a tooth-colored or transparent dental composite material shaped to desired contours or premolded standardized buttons may be bonded to the teeth using dental adhesives.

Directing attention now to FIG. 20, button 91 is bonded to the facial surface of a central incisor and button 92 to the lingual surface. Both buttons 91, 92 have beveled edges 93 on each of their four rectangular sides Additionally, a transverse groove 94 is formed in each of the buttons 91, 92 into which a tongue (not shown) of the cap or tooth clasping portion 37 fits for more effective gripping action. It will be understood that the buttons 91, 92 shown in FIGS. 20 and 20A may be used with any of the preceding modifications which are shown to interact with such buttons in the preceding and following modifications. The same applies to those modified buttons shown in FIGS. 21-25. FIG. 20C shows the buttons 91, 92 applied to a bicuspid and FIG. 20D shows the same applied to a molar. It will be understood that the same or similar buttons may be applied to all of the teeth in a particular patient's mouth.

Figure 21E:
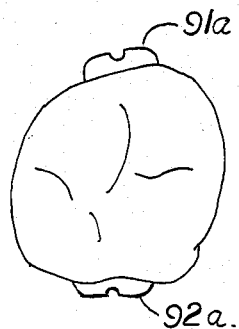
FIG. 21E is a view similar to FIG. 20D showing the modification of FIG. 21.

FIG. 21 shows buttons 91a and 92a applied to an incisor. Such buttons differ from those in FIG. 20 in that there is a longitudinal groove 96 formed in the button 21a and intersecting transverse groove 97, at least in the button 91a and preferably in the button 92a (although not shown in FIG. 21B). The cross channel 97 is optional. The vertical channel 96 provides parallel walls to prevent twisting. As shown in FIGS. 21C and 21B, the ends of buttons 91a and 91b have flat undercuts 98 near the gum line to provide for retention. It will be noted in FIG. 21 that the edges of the buttons 91a and 91b are not beveled but beveling as in FIG. 20 is optional.

Figure 22:
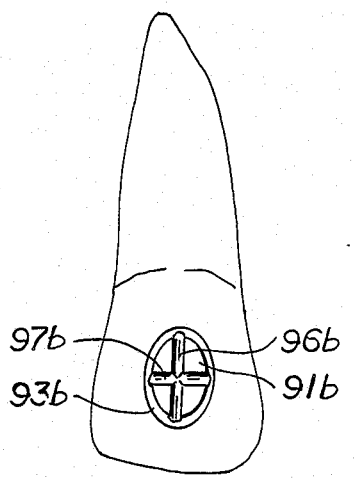
FIG. 22 is a view similar to FIG. 20 of a still further modification.
Figure 22A:
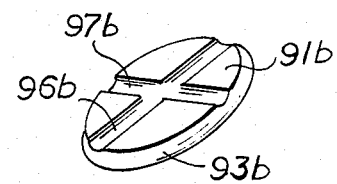
FIG. 22A is a view similar to FIG. 20B of the modification of FIG. 22.

In FIGS. 22 and 22A, an oval button 91b is provided having beveled edges 93b. Such button preferably has longitudinal and transverse grooves 96b and 97b respectively. Although shown applied only to the facial side of the incisor in FIG. 22, it will be understood the same button may be applied to the incisors, bicuspids and molars, as in the preceding modifications.

Figure 23A:
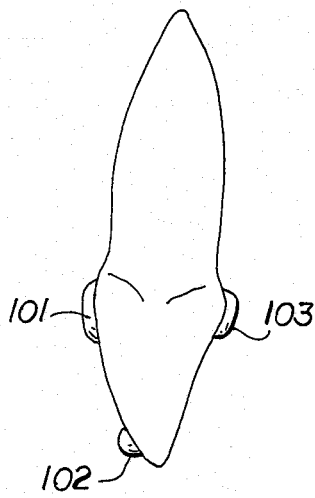
FIG. 23A is a view similar to FIG. 20A of the modification of FIG. 23.
Figure 23:
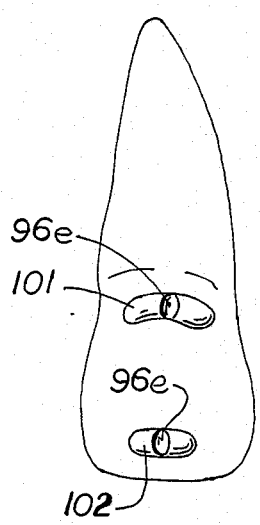
FIG. 23 is a view similar to FIG. 20 of a still further modification.
Figure 23B:
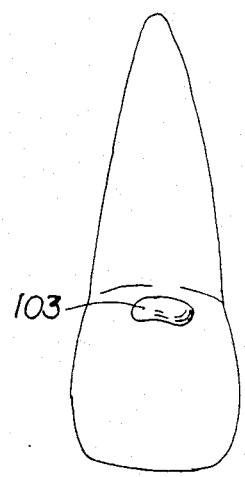
FIG. 23B is a lingual or rear elevational view of the structure of FIG. 23.

Turning now to FIGS. 23, 23A and 23B on the facial side of the incisor there is shown upper and lower buttons 101 and 102, and on the lingual side at least an upper button 103 (the lower button being optional). Each of the buttons is oval with its longest axis horizontal. Preferably at least on the facial side, buttons 101 and 102 are formed with vertical grooves 96c. No groove is shown in FIG. 23B, but such a groove is optional.

Figure 24:
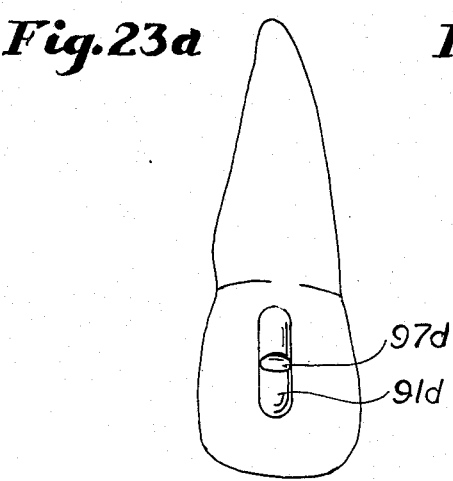
FIG. 24 is a view similar to FIG. 20 of another modification.
Figure 24A:
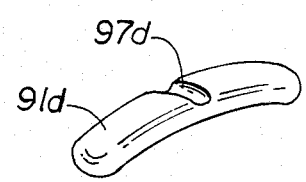
FIG. 24A is a view similar to FIG. 20B of the modification of FIG. 24.

FIGS. 24 and 24A show oval buttons 91d at least on the facial side of each of the teeth, the buttons being formed with transverse grooves 97d. The ends of the buttons 91d are preferably rounded. Bevelling of the lateral sides of the buttons is optional, parallel lateral sides being preferable.

FIGS. 25, 25A, 25B, 25C and 25D show buttons 91e and 92e which are generally square in shape having beveled edges 93e.

FIG. 26 shows a button 91f applied to the facial side of an incisor. Button 91f is in the shape of a trapezoid with its short parallel side uppermost. Preferably the edges 93f are beveled, but optionally one or more sides may be rounded and/or bevelled.

It will be understood that the modifications of FIGS 20-25 are interrelated and that the buttons may be applied not only to the incisors but to bicuspids and molars and may be applied to both the facial and lingual surfaces of the teeth or to only the facial or lingual surfaces of the teeth. Whereas in FIG. 23 there are shown buttons 101 and 102 in upper and lower position on the teeth, it will be understood that all of the buttons shown in the drawings of the accompanying application may be placed both in upper and lower positions but are of shapes such as shown in FIGS. 4, 20-22 and 24-26.

Figure 10:
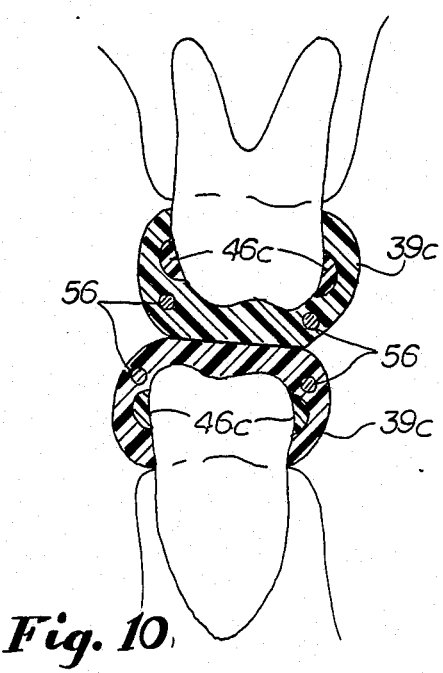
FIGS. 8, 9 and 10 are views similar to FIGS. 1, 2 and 3 of another modification.
Figure 9:
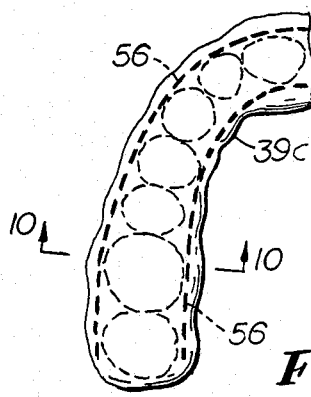
Figure 8:
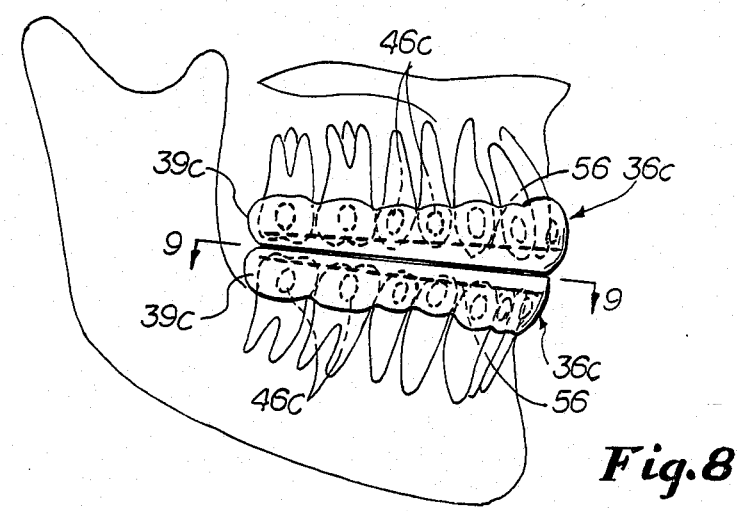

In the modification of FIGS. 8-10, flexible intermediate portion 39c is molded directly to adapt to the tooth surfaces with bonded buttons 46c attached as in the modification of FIG. 4. This forms a flexible clasp which fits over the button 46c on the tooth. Rather than providing a backbone similar to that shown in FIGS. 1-3 that is flat and forms the biting surface of the appliance, a material such as a plurality of metal wires 56 is imbedded in the intermediate portion 39c to provide the required additional stiffness to selected portions of the appliance to correct certain types of dental misalignments or to hold certain groups of teeth in their approximately present position. Wires 56 assist in controlling the properties of the appliance such as stiffness, flexibility and the like in various directions. The springiness of the tooth clasping surfaces of the appliance may be controlled in this manner. For example, if it is desired to expand the arch width at the molars, a metal wire or wires significantly increases the force applied at the posterior extremities of the appliance while still allowing the appliance to be seated over the teeth. Wires 56 may be bent after the appliance is made to provide additional force beyond what is available which had been made for a given arch width. E.g., the dentist may bend the wire beyond the desired ultimate position and then alter the wire shape before the teeth overshoot the desired position.

In the modification of FIGS. 8A-10A, rectangular wire reinforcements 48 of fiber, carbon or various plastics or metals may be used. FIGS. 8B-10B show a mesh of wire 59 used as a reinforcement. This mesh may be glass fiber or metal or other materials.

The modifications of FIGS. 8A-10A and FIGS. 8B-10B resemble that of FIGS. 8-10 and the same reference numerals followed by the subscripts g and h, respectively, are used to designate corresponding elements.

Figure 11:
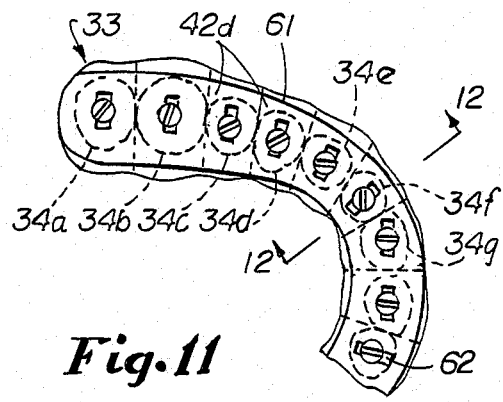
FIGS. 11 is a somewhat schematic view further modification.
Figure 12:
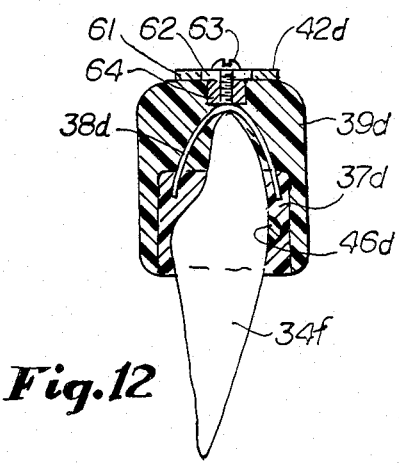
FIG. 12 is a sectional view taken substantially along the line 12—12 of FIG. 11.

Directing attention now to the modification of the invention shown in FIGS. 11 and 12, an attachment to the forms of the invention previously described is shown. In FIG. 11 such attachments are applied to each of the teeth but it will be understood that in actual practice the attachments would be used only with a single tooth or a few teeth rather than being distributed throughout the entire dental arch.

Thus, as shown in FIGS. 11 and 12, a plate 61 serves as the backbone for this modification and is connected to intermediate flexible plastic portions 39f for each tooth. In those locations where special treatment of the teeth is required such as to correct a tipping problem malocclusion of an incisor 34f, a slot 62 is formed in plate 61, the direction of the slot being the direction of desired movement of the tooth. An adjustment screw 63 fits through the slot 62 and into a reinforcement or screw socket 64 which is fixed in the flexible intermediate portion 39d for the particular tooth in question. By loosening the screw 63 periodically and gradually moving the intermediate portion 39d in the desired direction and then retightening the screw 63, over a period of time the malocclusion may be corrected.

In the preferred embodiment best shown in FIG. 12, plastic buttons 46d are fixed to the tooth 34f. The rigid tooth clasp portion 37d removably fits over the button 46d and is preferably reinforced by spring clips 38d imbedded in the flexible intermediate portion 39d. Due to additional appliance thickness required to accommodate the adjustment screw, the modification of FIGS. 11-12 is best applied to anterior teeth where the appliance is normally thicker anyway. In locations where slots 62 are not located (i.e., in locations where large adjustments of the position of the tooth is not required) the structure underlying the plate 61 may be similar to that in the previous modifications hereinbefore described.

Figure 13B:
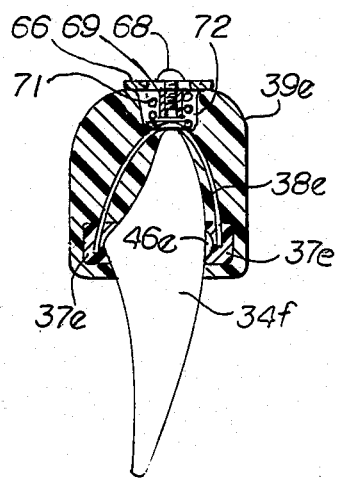
FIGS. 13B, 13C and 13D show the device of FIG. 13A in different positions of adjustment

FIG. 13b shows a modification of FIG. 12. The tooth clasping portion made up of the caps 37e (which fit over buttons 46) and the spring clips 38 is connected via a coil spring 71 to a threaded socket 69, the coil spring serving as the intermediate portion for this variation.

Figure 14:
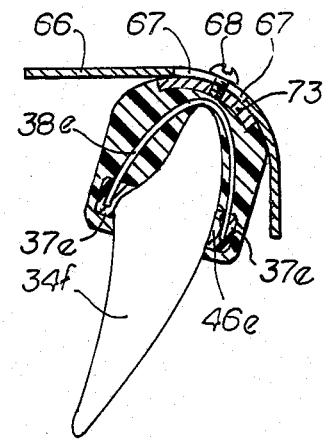
FIGS. 14 and 15 are views similar to FIG. 12 of additional modifications.
Figure 15:
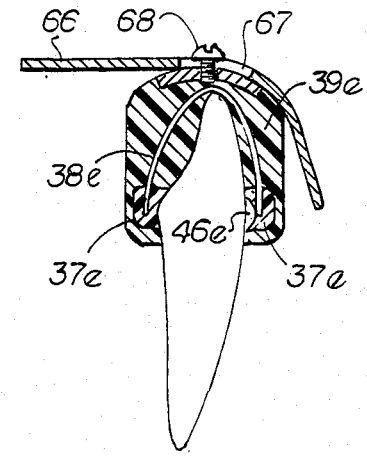
Figure 8A:
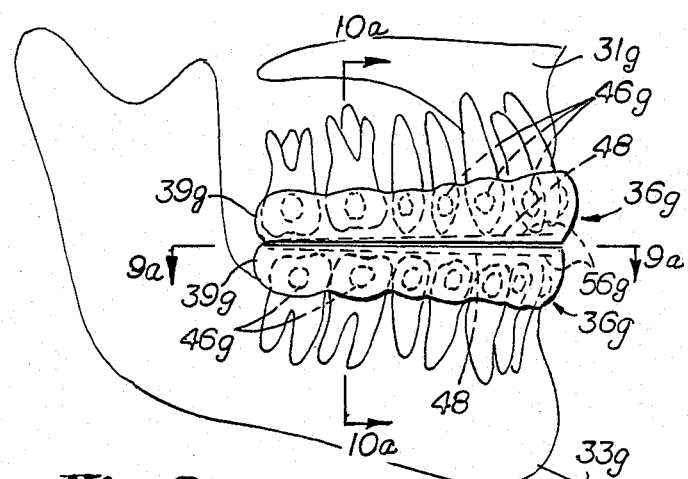
FIGS. 8A, 9A and 10A are views similar to FIGS. 1, 2 and 3, respectively, of a further modification.
Figure 10A:
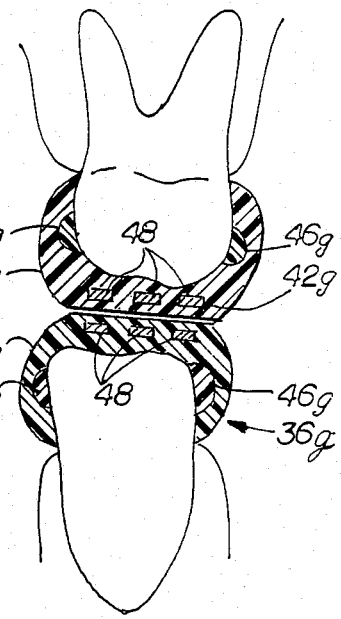
Figure 9A:
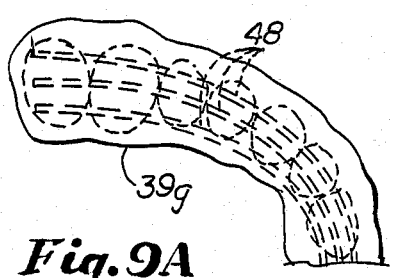
Figure 8B:
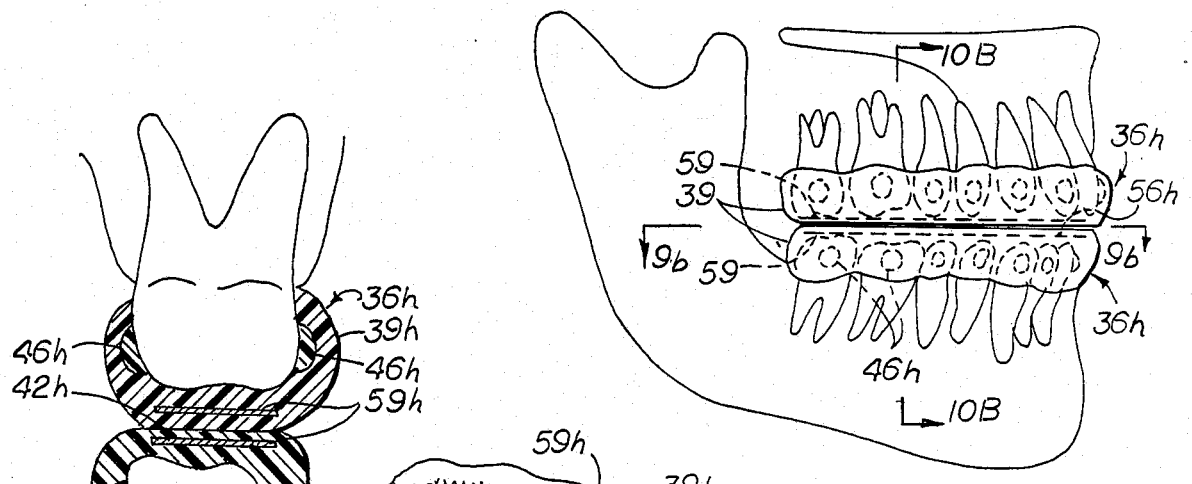
FIGS. 8B, 9B and 10B are views similar to FIGS. 1, 2 and 3, respectively, of another modification.
Figures 9B, 10B:
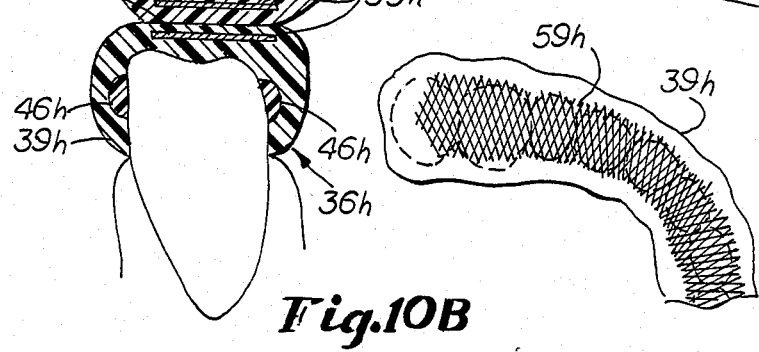

FIGS. 14 and 15 show another modification of the appliance shown in FIGS. 11 and 12. In a case where a tooth is tipped more than the flexibility of the appliance will allow, or where the orthodontist desires to tip a tooth or a group of teeth, the backbone 66 of the appliance may be curved as shown in FIGS. 14 and 15. The desired radius of curvature and the center of curvature are dependent upon the desired tooth movement.

In FIG. 14, the tooth clasping portion of the appliance made up of caps 37e (over buttons 46 bonded to the enamel surface) connected by spring clips 38e are imbedded in the intermediate material 39e. The intermediate material 39e is movably connected to the backbone 66 by a screw 68 threaded into a curved reinforcing plate 73. The plate 73 is rigidly attached to the intermediate material. The intermediate material may be moved periodically relative to the backbone 66 by loosening the screw, moving the intermediate material a short distance along the curved slot 67 and retightening the screw. The curved reinforcing plate 73 provides a surface for sliding the intermediate material and prevents tearing the weaker intermediate material. The reinforcing plate also contains threads to engage the screw 68.

The spring 71 of FIG. 13 provides additional range of adjustment of the appliance. It allows the tooth-clasping portion of the appliance to be applied to teeth farther out of line than in the preceding modifications.

Figure 13C:
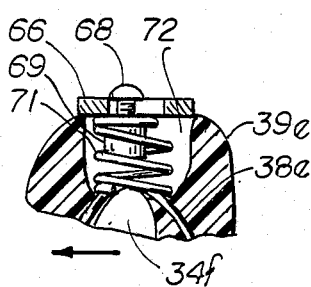
Figure 13A:
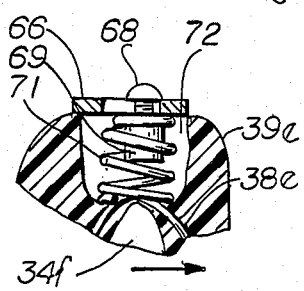
FIG. 13A is a view similar to FIG. 12 of a modification.
Figure 13D:
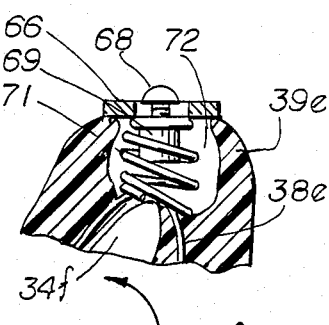

Directing attention to FIG. 13A, with the spring 71 in the position shown relative to screw 68, the spring moves the tooth to the right (in the direction of the arrow). In FIG. 13B, the coil of spring 71 is centered and the tooth is upright so that there is no side force on the coil. FIG. 13C shows the spring in the position opposite FIG. 13A and in this position the spring moves the tooth to the left, as viewed therein. FIG. 13D shows a badly tipped tooth. The spring has an uprighting force placed on it by reason of the location of the spring.

Figure 16:
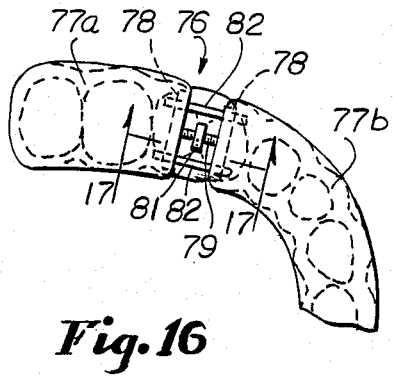
FIG. 16 is a view similar to FIG. 2 of still another modification.
Figure 17:
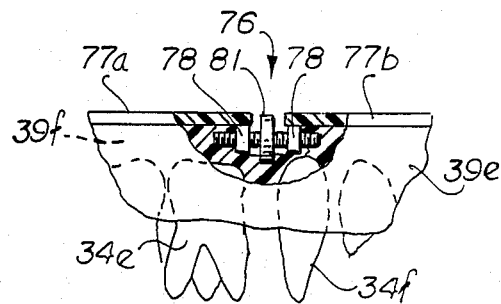
FIG. 17 is an enlarged sectional view taken substantially along the line 17—17 of FIG. 16.

In the modification shown in FIGS. 16 and 17, any of the clasp assemblies previously described for other appliance variations may be used and the various intermediate portions may also be used. Two separated rigid metal or plastic plates 77a and 77b are attached to the underlying intermediate portion 39f, there being a gap between the adjacent edges of the plates 77a, 77b. At the area adjacent the separation, the plates 77a, 77b are formed with downturned ears 78. A screw 79 having oppositely threaded ends is threaded into holes in the ears 78 and provided with a head 81 which, when turned, causes the screw 79 to turn and to draw the ears 78 toward or away from each other depending upon the direction of turning of the head 81. Movement of the ears 78 causes corresponding movement of the plate section 77a, 77b and consequently movement of the teeth engaged thereby. To guide the movement more positively, one or more guide pins 82 parallel to screw 79 may be used extending through holes in the ears 78.

Figure 18:
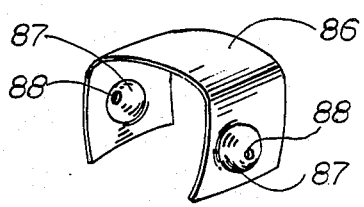
FIG. 18 is a perspective view of a modified clasp.
Figure 19:
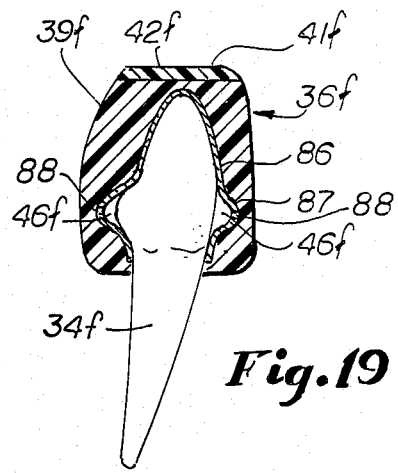
FIG. 19 is a sectional view through a tooth with the clasp of FIG. 18 in place.

FIG. 18 shows an improved clasp. A shell 86 is stamped of thin metal or other suitable material, preformed complementary to the tooth 34f to which it is to be applied. The shell 86 may be custom shaped to fit the patient's tooth or may be a stock component. On opposite sides of shell 86 are convex dimples 87 and in each dimple 87 is a locating hole 88. The shell 86 is initially placed on the tooth 34f and a marking tool is inserted through each hole 88 to place a locating mark on the tooth. Buttons 46f are then centered relative to the markings and fixed to the tooth.

The shell 86 is then molded into the appliance 36f. The dimples 87 snap over the buttons 46f to secure the appliance 36f to the tooth 34f.

The various modifications set forth in this specification employ tooth clasping portions engaging the natural contour of the teeth or an enhancement of such contour (e.g. buttons fixed to the teeth). Where buttons are used, the inner surface of the tooth clasping portions fit closely the contour of whatever button is used. Thus, as used in the claims, the term "tooth clasp portion" comprises a fairly rigid member which engages the undercut of the tooth or a button fixed to the tooth and may include a rigid cap which fits over a button and may have one or more tongues which engage one or more grooves in the button.

What is claimed is:

1. An appliance for othodonture characterized in that at least most of said appliance may be installed and removed by the patient as required, said appliance comprising
    a tooth clasp portion having individual clasps shaped to grip individual teeth while in malocclusion positions and being relatively rigid,
    a resilient intermediate portion overlying and fixed to said tooth clasp portion,
    a backbone portion of construction more rigid than said intermediate portion fixed to said intermedite portion and shaped to stress said intermediate portion so as to bias said clasp portion from an initial malocclusion position toward a desired ideal position,
    said tooth clasp portion, said intermediate portion and said backbone portion being contained within a single appliance shaped to fit upon at least a portion of one jaw of a patient.

2. An appliance according to claim 1 in which each of said portions is of a different material.

3. An appliance according to claim 1 which further comprises a plurality of spring tension wires of U-shape having a central part imbedded in said intermediate portion and inwardly biased ends engaging said clasp portion on opposite surfaces of the teeth to hold said clasp portion in tight engagement with the teeth, said wires extending over the occlusal surfaces of the teeth.

4. An appliance for orthodonture characterized in that at least most of said appliance may be installed and removed by the patient as required, said appliance comprising
    a tooth clasp portion having individual clasps shaped to grip individual teeth while in malocclusion position and being relatively rigid,
    a resilient intermediate portion overlying and fixed to said tooth clasp portion,
    a backbone portion of construction more rigid than said intermediate portion fixed to said intermediate portion and shaped to stress said intermediate portion so as to bias said clasp portion from an initial malocclusion position toward a desired ideal position, and at least one rigid button shaped to be continuously attached to a tooth after the appliance is temporarily removed, said tooth clasp portion being shaped to engage said button.

5. An appliance according to claim 4 which further comprises a cap imbedded in said tooth clasp portion, said cap being shaped to tightly engage said button.

6. An appliance according to claim 5 which further comprises cooperating interlocking means on the interfitting surfaces of said cap and button to enhance engagement of said cap and button.

7. An appliance according to claim 4 in which said button is a vertically elongated rectangle.

8. An appliance according to claim 7 which further comprises a second button on the surface of said tooth opposite said first-mentioned button.

9. An appliance according to claim 7 in which the edge of said button are beveled.

10. An appliance according to claim 7 in which the ends of said button are formed with rounded corners.

11. An appliance according to claim 7 in which said button is formed with a vertical groove for better engagement with said tooth clasp portion.

12. An appliance according to claim 11 in which said button is formed with a transverse groove intersecting said vertical groove.

13. An appliance according to claim 7 in which the corners of said rectangle are rounded to an ellipsoid shape.

14. An appliance according to claim 4 in which said button is located near the gum line on the facial side of said tooth and which further comprises a second button on said facial side remote from said first-mentioned button.

15. An appliance according to claim 14 in which at least one of said buttons is transversely elongated with rounded ends.

16. An appliance according to claim 15 in which at least one said button is formed with a vertical groove for better engagement with said tooth clasp portion.

17. An appliance according to claim 14 which further comprises a third button on the lingual side of said tooth.

18. An appliance according to claim 4 in which said button is a vertically elongated oval and is formed with a transverse groove for better engagement with said tooth clasp portion.

19. An appliance according to claim 18, said button having parallel vertical sides.

20. An appliance according to claim 18, in which said sides are bevelled.

21. An appliance according to claim 4 in which said button is an approximately square rectangle.

22. An appliance according to claim 21 in which the edges of said button are beveled.

23. An appliance according to claim 4 in which said button is a trapezoid with the shorter parallel side closer to the gum line.

24. An appliance according to claim 23 in which the edges of said buttons are beveled.

25. An appliance according to claim 1 in which said intermediate and backbone portions are formed of a single piece of material.

26. An appliance according to claim 1 in which said backbone portion comprises stiffening means imbedded within said intermediate portion.

27. An appliance according to claim 26 in which said stiffening means comprises wire.

28. An appliance according to claim 26 in which said stiffening means comprises glass fiber mesh.

29. An appliance according to claim 25 in which there are two round wires located on opposite sides of said appliance.

30. An appliance according to claim 25 in which there is at least one flat rectangular wire imbedded in said intermediate portion.

31. An appliance according to claim 25 in which there is a mesh imbedded in said intermediate portion.

32. An appliance according to claim 1 in which said backbone has a relatively flat outer surface comprising the occlusal surface of said appliance.

33. An appliance according to claim 1 in which said backbone is formed with at least one slot, a screw through said slot, a socket imbedded in said intermediate portion threaded to receive said screw and means extending from said intermediate portion into said clasp portion to bias a tooth engaged by said clasp portion in the direction of movement of said screw along said slot.

34. An appliance according to claim 33 in which said backbone portion and said slot formed therein are curved, the intermediate portion and underlying clasp portion for a single tooth being a section discrete from the remainder of the appliance in the region where said backbone is curved to allow said section to be moved over time in a curved path to correct tooth tipping problem malocclusion.

35. An appliance according to claim 34 which further comprises resilient means between said socket and said clasp portion to bias said clasp portion to correct said tooth.

36. An appliance according to claim 35 in which said clasp portion comprises first and second caps securely engaging the facial and lingual surfaces of said tooth and said resilient means comprises at least one resilient spring tension wire of approximately U-shape fixed at either end to one of said caps.

37. An appliance according to claim 36 in which said resilient means further comprises a coil spring around said socket, said coil spring being fixed at a first end to said socket and a second end to the middle of said spring tension wire.

38. An appliance according to claim 37 in which said intermediate portion surrounds said socket and said coil spring.

39. An appliance according to claim 1 in which said appliance is divided into at least two sections with a gap between said sections and which further comprises an adjustable expansion member bridging said gap and having opposite ends anchored to one of said sections, said expansion member having adjustment means to bring said opposite ends closer together or farther apart.

40. An appliance according to claim 39 which further comprises cooperating alignment means on said sections to move said sections relative to each other in alignment.

41. An appliance according to claim 39 in which said expansion member comprises first and second members having first and second ears, respectively, imbedded in opposite sections of said appliance, said ears being threaded, a screw having opposite threads at opposite ends threaded into said ears and means for turning said screw and thereby drawing said members closer or spreading said members farther apart.

42. An appliance according to claim 41 which further comprises alignment means between said ears to move said members parallel to each other.

43. An appliance according to claim 1 which further comprises at least one rigid button continuously attached to a tooth and in which said clasp portion comprises a thin shell of metal or the like shaped to fit over the tooth, said shell being formed with a convex dimple complementary to each said button.

44. A method of orthodonture comprising forming casts of upper and lower teeth of the patient with at least some teeth in malocclusion position;
locating the hinge axis of the jaws of the patient;
forming duplicate casts of said first-mentioned casts;
mounting said duplicate casts in an articulator simulating the jaw movements of the patient about said hinge axis;
cutting apart each duplicate cast into an individual teeth;
arranging the individual teeth in desired ideal position and holding the individual teeth in place;
providing an appliance comprising
a tooth clasp portion having individual clasps shaped to grip individual teeth while in malocclusion positions and being relatively rigid,
a resilient intermediate portion overlying and fixed to said tooth clasp portion, and
a backbone portion of construction more rigid than said itnermediate portion fixed to said intermediate portion and shaped to stress said intermediate portion so as to bias said clasp portion from an initial malocclusion position toward a desired ideal position, such appliance being shaped to said teeth in ideal position whereby said clasp portion engages securely each tooth and said intermediate portion is un-stressed; and
applying said appliance to the jaws of the patient, said appliance being stressed because of pre-existing malocclusion and the resilient material of said appliance biasing said teeth toward ideal position.

* * * * *